US010993969B2

(12) United States Patent
Petrucci

(10) Patent No.: US 10,993,969 B2
(45) Date of Patent: May 4, 2021

(54) METHODS AND MATERIALS FOR TREATING NERVE INJURIES AND NEUROLOGICAL DISORDERS

(71) Applicant: Gary M. Petrucci, Long Lake, MN (US)

(72) Inventor: Gary M. Petrucci, Long Lake, MN (US)

( * ) Notice: Subject to any disclaimer, the term of this patent is extended or adjusted under 35 U.S.C. 154(b) by 0 days.

(21) Appl. No.: 15/567,160

(22) PCT Filed: Feb. 2, 2017

(86) PCT No.: PCT/US2017/016225
§ 371 (c)(1),
(2) Date: Oct. 17, 2017

(87) PCT Pub. No.: WO2017/136557
PCT Pub. Date: Aug. 10, 2017

(65) Prior Publication Data
US 2018/0338998 A1    Nov. 29, 2018

Related U.S. Application Data

(60) Provisional application No. 62/292,009, filed on Feb. 5, 2016, provisional application No. 62/293,866, filed on Feb. 11, 2016.

(51) Int. Cl.
| | | |
|---|---|---|
| *A61K 35/50* | (2015.01) |
| *A61K 35/12* | (2015.01) |
| *A61L 27/36* | (2006.01) |
| *A61L 27/50* | (2006.01) |
| *A61K 35/28* | (2015.01) |
| *A61L 27/38* | (2006.01) |

(52) U.S. Cl.
CPC ............. *A61K 35/50* (2013.01); *A61K 35/12* (2013.01); *A61K 35/28* (2013.01); *A61L 27/3604* (2013.01); *A61L 27/3675* (2013.01); *A61L 27/3683* (2013.01); *A61L 27/3834* (2013.01); *A61L 27/3878* (2013.01); *A61L 27/507* (2013.01); *A61L 2400/06* (2013.01); *A61L 2430/32* (2013.01); *A61L 2430/40* (2013.01)

(58) Field of Classification Search
CPC ................................................. A61L 27/3406
See application file for complete search history.

(56) References Cited

U.S. PATENT DOCUMENTS

| | | | |
|---|---|---|---|
| 4,828,844 A | 5/1989 | Rontgen-Odenthal et al. |
| 5,049,389 A | 9/1991 | Radhakrishnan |
| 5,524,462 A | 6/1996 | Loughlin |
| 5,656,498 A | 8/1997 | Iijima et al. |
| 5,674,192 A | 10/1997 | Sahatijan et al. |
| 7,524,489 B2 | 4/2009 | Messina et al. |
| 7,682,803 B2 | 3/2010 | Paludan |
| 8,323,701 B2 | 12/2012 | Daniel et al. |
| 8,357,403 B2 | 1/2013 | Daniel et al. |
| 8,372,437 B2 | 2/2013 | Daniel |
| 8,372,438 B2 | 2/2013 | Daniel et al. |
| 8,372,439 B2 | 2/2013 | Daniel et al. |
| 8,409,626 B2 | 4/2013 | Daniel et al. |
| 8,460,715 B2 | 6/2013 | Daniel |
| 8,460,716 B2 | 6/2013 | Daniel |
| 8,623,421 B2 | 1/2014 | Daniel |
| 8,642,092 B2 | 2/2014 | Daniel et al. |
| 8,703,206 B2 | 4/2014 | Daniel et al. |
| 8,703,207 B2 | 4/2014 | Daniel et al. |
| 8,709,493 B2 | 4/2014 | Daniel et al. |
| 8,709,494 B2 | 4/2014 | Daniel |
| 8,904,664 B2 | 12/2014 | Pringle et al. |
| 8,932,643 B2 | 1/2015 | Daniel et al. |
| 9,039,783 B2 | 5/2015 | Petter-Puchner |
| 9,080,184 B2 | 7/2015 | Kharazi et al. |
| 9,084,767 B2 | 7/2015 | Daniel et al. |
| 9,180,145 B2 | 11/2015 | Brown et al. |
| 9,186,382 B2 | 11/2015 | Daniel et al. |
| 9,205,177 B2 | 12/2015 | Schorgl et al. |
| 9,265,800 B2 | 2/2016 | Daniel |
| 9,265,801 B2 | 2/2016 | Daniel |
| 9,272,003 B2 | 3/2016 | Daniel et al. |
| 9,272,005 B2 | 3/2016 | Daniel |
| 9,415,074 B2 | 8/2016 | Daniel et al. |
| 9,433,647 B2 | 9/2016 | Daniel |
| 9,463,206 B2 | 10/2016 | Koob et al. |
| 9,533,011 B2 | 1/2017 | Daniel et al. |
| 9,555,062 B2 | 1/2017 | Pringle et al. |
| 9,572,839 B2 | 2/2017 | Daniel |
| 9,655,948 B1 | 5/2017 | Koob et al. |
| 9,662,355 B2 | 5/2017 | Koob et al. |
| 9,687,588 B2 | 6/2017 | Daniel et al. |
| 9,789,137 B2 | 10/2017 | Daniel et al. |
| 9,827,293 B2 | 11/2017 | Koob et al. |
| 10,016,464 B2 * | 7/2018 | Murphy .............. A61L 27/3683 |

(Continued)

FOREIGN PATENT DOCUMENTS

| | | |
|---|---|---|
| WO | WO 98/08492 | 5/1998 |
| WO | WO 2007/038686 | 4/2007 |
| WO | WO 2012/088396 | 6/2012 |
| WO | WO 2012/112410 | 8/2012 |
| WO | WO 2014/047067 | 3/2014 |
| WO | WO 2015/134936 | 9/2015 |
| WO | WO 2016/007554 | 1/2016 |
| WO | WO 2016/198670 | 12/2016 |

OTHER PUBLICATIONS

Liu et al. Genetics and Molecular Research, 2014, 13(3)7990-8001.*
Derdeyn et al., "Collagen-Coated Acrylic Microspheres for Embolotherapy: In Vivo and In Vitro Characteristics," AJNR Am J Neuroradiol, Apr. 1997, 18:647-653.

(Continued)

*Primary Examiner* — Bin Shen
(74) *Attorney, Agent, or Firm* — Merchant & Gould P.C.

(57) ABSTRACT

This document provides methods and materials for treating nerve injuries and/or neurological disorders. For example, compositions including an amnion tissue preparation and/or a stem cell preparation as well as methods for using such compositions to treat a nerve injuries and/or neurological disorders are provided.

16 Claims, No Drawings

(56) References Cited

U.S. PATENT DOCUMENTS

| | | |
|---|---|---|
| 2003/0187515 A1 | 10/2003 | Hariri |
| 2003/0229394 A1 | 12/2003 | Ogle et al. |
| 2003/0235563 A1 | 12/2003 | Strom et al. |
| 2003/0235580 A1 | 12/2003 | Zhang |
| 2004/0147045 A1 | 7/2004 | Nelson |
| 2005/0020500 A1 | 1/2005 | Shen et al. |
| 2005/0287223 A1 | 12/2005 | Peyman |
| 2007/0031471 A1 | 2/2007 | Peynnan |
| 2007/0293872 A1 | 12/2007 | Peyman |
| 2008/0181950 A1 | 7/2008 | Bates |
| 2009/0125044 A1 | 5/2009 | Lary |
| 2009/0238801 A1 | 9/2009 | Woodbury et al. |
| 2009/0270978 A1 | 10/2009 | Virkler |
| 2010/0143312 A1 | 6/2010 | Hariri |
| 2010/0228335 A1 | 9/2010 | Schorgl |
| 2010/0260721 A1 | 10/2010 | McGonagie |
| 2011/0307003 A1 | 12/2011 | Chambers |
| 2012/0080030 A1 | 4/2012 | Wachter |
| 2012/0171171 A1 | 7/2012 | West et al. |
| 2012/0201787 A1 | 8/2012 | Abbot et al. |
| 2012/0026785 A1 | 10/2012 | Woods et al. |
| 2013/0071358 A1 | 3/2013 | Peterson |
| 2014/0236161 A1 | 8/2014 | Brahm |
| 2014/0271776 A1 | 9/2014 | Vines |
| 2015/0037436 A1 | 2/2015 | Huang et al. |
| 2015/0216910 A1 | 8/2015 | Horton et al. |
| 2015/0216912 A1 | 8/2015 | Koob |
| 2016/0136334 A1 | 5/2016 | Schorgl et al. |
| 2016/0193253 A1 | 7/2016 | Petrucci |
| 2016/0193254 A1 | 7/2016 | Petrucci |
| 2016/0199417 A1 | 7/2016 | Werber |
| 2017/0042943 A1 | 2/2017 | Namin et al. |

OTHER PUBLICATIONS

Harvard Men's Health Watch, "The crucial, controversial carotid artery Part I: The artery in health and disease," Harvard Health Publishing, Aug. 2011, 6 pages.

International Preliminary Report on Patentability in International Application No. PCT/US2017/016225, dated Aug. 16, 2018, 7 pages.

International Search report and Written Opinion in International Application No. PCT/US 18/38815, dated Sep. 19, 2018, 16 pages.

Robertson et al., "Angioplasty and stenting for peripheral arterial disease of the lower limbs: an overview of Cochrane Reviews (Protocol)," Cochrane Database of Systematic Reviews, Feb. 2017, 2: CD012542 (11 pages).

"Angioplasty or bypass surgery?," Harvard Heart Letter, Apr. 2008, 2 pages.

Alkilani et al., "Transdermal Drug Delivery: Innovative Pharmaceutical Developments Based on Disruption of the Barrier Properties of the stratum corneum," Pharmaceutics, 2015, 7: 438-470.

Brown et al., "Dermal and Transdermal Drug Delivery Systems: Current and Future Prospects," Drug Delivery, 2006, 13: 175-187.

Chen et al., "The effects of acellular amniotic membrane matrix on osteogenic differentiation and ERK1/2 signaling in human dental apical papilla cells," Biomaterials, 2012, 33(2): 455-63.

Dhote et al., "Iontophoresis: A Potential Emergence of a Transdermal Drug Delivery System," Sci Pahrm, 2012, 80: 1-28.

Diaz-Prado et al., "Human amniotic membrane as an alternative source of stem cells for regenerative medicine," Differentiation, 2011, 81(3): 162-71.

Gerth et al., "Clinical outcomes for Conduits and Scaffolds in peripheral nerve repair," Worls J Clin Cases, Feb. 2015, 3: 141-147.

Hassan et al., "Neural-Differentiated Mesenchymal Stem Cells Incorporated into Muscle Stuffed Vein Scaffold Forms a Stable Living Nerve Conduit," Journal of Orthopaedic Research, Oct. 2012, 1674-1681.

International Preliminary Report on Patentability in Application No. PCT/US2015/068127, dated Jul. 11, 2017, 12 pages.

International Preliminary Report on Patentability in Application No. PCT/US2015/068136, dated Jul. 11, 2017, 11 pages.

International Search report and Written Opinion in International Application No. PCT/2017/016225, dated Apr. 14, 2017, 18 pages.

International Search Report and Written Opinion in International Application No. PCT/US2015/68127, dated Apr. 19, 2016, 18 pages.

International Search Report and Written Opinion in International Application No. PCT/US2015/68136, dated Feb. 26, 2016, 13 pages.

Kalluri and Banga, "Transdermal Delivery of Proteins," AAPS PharmSciTech, Mar. 2011, 12: 431-441.

Khan et al., "Iontophoretic drug delivery: History and applications," Journal of Applied Pharmaceutical Science, 2011, 11-24.

Kumar and Philip, "Modified Transdermal Technologies: Breaking the Barriers of Drug Permeation via the Skin," Tropical Journal of Pharmaceutical research, Mar. 2007, 6: 633-644.

Lei et al., "Dehydrated Human Amnion/Chorion Membrane (dHACM) Allografts as a Therapy for Orthopedic Tissue Repair," Techniques in Orthopaedics, 2017, 9 pages.

McDonald et al., "Maintenance of human amnion epithelial cell phenotype in pulmonary surfactant," Stem Cell Research & Therapy, 2014, 5: 107.

Orth et al., "Current perspectives in stem cell research for knee cartilage repair," Stem Cells Cloning, Jan. 2014, 7: 1-17.

Quint et al., "Decellularized tissue-engineered blood vessel as an arterial conduit," PNAS, May 2011, 108: 9214-9219.

Sabongi et al., "Peripheral nerve regeneration with conduits: use of vein tubes," Neural regen Res, Apr. 2015, 10: 529-533.

Vaidya et al., "An Overview of Embolic Agents," Seminars in Interventional Radiology, 2008, 25: 204-215.

Wilshaw et al., "Production of an acellular amniotic membrane matrix for use in tissue engineering," Tissue Eng., 2006, 12(8): 2117-29.

Zhan et al., "Nanofiber scaffolds facilitate functional regeneration of peripheral nerve injury," Nanomedicine, 2013, 9: 305-315.

Liu, "[Shunt tube implantation combining amniotic membrane transplantation and implantation of Molteno implant for glaucoma after penetrating keratoplasty]," Yan Ke Xue Bao, Jun. 2000, 16: 65-72, Abstract Only.

Anand et al., "Use of amniotic membrane graft in glaucoma shunt surgery," Opthalmic Surg Lasers Imaging, May-Jun. 2011, 42: 184-9.

\* cited by examiner

METHODS AND MATERIALS FOR TREATING NERVE INJURIES AND NEUROLOGICAL DISORDERS

CROSS REFERENCE TO RELATED APPLICATIONS

This application is a National Stage Application under 35 U.S.C. § 371 and claims the benefit of International Application No. PCT/US2017/016225, filed Feb. 2, 2017, which claims the benefit of U.S. Provisional Application Ser. No. 62/292,009, filed Feb. 5, 2016, and U.S. Provisional Application Ser. No. 62/293,866, filed Feb. 11, 2016, the content of which Applications are incorporated herein by reference in their entirety.

BACKGROUND

1. Technical Field

This document relates to methods and materials for treating nerve injuries and/or neurological disorders. For example, this document provides methods and materials for using compositions (e.g., injectable formulations) that include an amnion tissue preparation and/or a stem cell preparation to treat nerve injuries and/or neurological disorders.

2. Background Information

Nerves are fragile and can be damaged by pressure, stretching, or cutting. Injury to a nerve can stop signals to and from the brain, causing muscles not to work properly, and a loss of feeling in the injured area. In addition, hundreds of millions of people worldwide are affected by neurological disorders. Approximately 6.2 million people die because of stroke each year. It is estimated that there are globally 35.6 million people with dementia with 7.7 million new cases every year.

SUMMARY

This document provides compositions that include an amnion tissue preparation and/or a stem cell preparation. Such compositions can be formulated for injection and used to treat nerve injuries (e.g., spinal cord injury) and/or neurological disorders (e.g., brain trauma, stroke, or dementia). This document also provides methods for using an amnion tissue preparation, a stem cell preparation, or both in combination to treat nerve injuries (e.g., spinal cord injury) and/or neurological disorders (e.g., brain trauma, stroke, or dementia).

In general, one aspect of this document features a method of treating a nerve injury or a neurological disorder in a mammal. The method comprises, or consists essentially of, administering, to the mammal, an amnion tissue preparation lacking viable cells and a stem cell preparation having viable cells, wherein a symptom of the a nerve injury or neurological disorder is improved. The mammal can be a human, dog, or horse. The method can comprise treating the nerve injury, and the nerve injury is a spinal cord injury or a peripheral nerve injury. The method can comprise treating the nerve injury, and the nerve injury is a partially or fully severed nerve. The method can comprise treating the neurological disorder, and the neurological disorder is selected from the group consisting brain trauma, stroke, and dementia. The amnion tissue preparation can be administered by injection into a neurological tissue of the mammal. The stem cell preparation can be administered by injection into a neurological tissue of the mammal. The method can further comprise monitoring the nerve injury or neurological disorder of the mammal. The amnion tissue preparation can comprise an amnion tissue preparation prepared from about 1 mg to about 10 g of amnion tissue per kg of body weight of the mammal. The stem cell preparation can comprise from about 0.3 million to about 3 million stem cells per kg of body weight of the mammal. The amnion tissue preparation can be a human amnion tissue preparation. The stem cell preparation can be a human mesenchymal stem cell preparation. The stem cell preparation can be a human neural stem cell preparation.

In another aspect, this document features a composition comprising a blood vessel conduit, a stem cell preparation having viable cells, and an amnion tissue preparation. The blood vessel conduit can be a vein. The blood vessel conduit can be an artery. The amnion tissue preparation can comprise viable cells. The amnion tissue preparation can lack viable cells. The stem cell preparation can be a human mesenchymal stem cell preparation. The stem cell preparation can be a human neural stem cell preparation. The composition can further comprise a therapeutic agent, an immunosuppressant agent, or a pharmaceutical excipient. The composition can comprise from about 5 mg and about 5 g of the amnion tissue preparation. The composition can comprise from about 10 mg and about 1 g of the amnion tissue preparation. The stem cell preparation can comprise from about 10 million to about 100 million stem cells.

In another aspect, this document features a nerve scaffold comprising a composition comprising a stem cell preparation having viable cells and an amnion tissue preparation. The nerve scaffold can comprise a blood vessel. The blood vessel can be a vein. The blood vessel can be an artery. The amnion tissue preparation can comprise viable cells. The amnion tissue preparation can lack viable cells. The stem cell preparation can be a human mesenchymal stem cell preparation. The stem cell preparation can be a human neural stem cell preparation. The nerve scaffold can further comprise a therapeutic agent, an immunosuppressant agent, or a pharmaceutical excipient. The composition can comprise from about 5 mg and about 5 g of the amnion tissue preparation. The composition can comprise from about 10 mg and about 1 g of the amnion tissue preparation. The stem cell preparation can comprise from about 10 million to about 100 million stem cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

This document provides methods and materials for treating nerve injuries (e.g., spinal cord injury) and/or neurological disorders (e.g., brain trauma, stroke, or dementia) using compositions that include an amnion tissue preparation (e.g., human amnion tissue preparation) and/or a stem cell preparation (e.g., a human stem cell preparation).

A nerve injury and/or neurological disorder can affect the central nervous system or the peripheral nervous system. The term "nerve injury" as used herein refers to any damage (e.g., crush, contusion, stretch, laceration, or severing) to a nervous tissue (e.g., nerve cells or neuroglia) causing an interruption in conduction of the impulse down the nerve fiber. Nerve injuries can include, without limitation, a spinal cord injury, a peripheral nerve injury, and a traumatic brain injury. The term "neurological disorder" as used herein refers to any condition that affects (e.g., directly or indirectly) the function of the nervous system. Neurological disorders can include, without limitation, brain trauma, stroke (e.g., ischemic stroke or hemorrhagic stroke), and dementia (e.g., Alzheimer's disease, vascular dementia, Lewy body dementia, or frontotemporal dementia).

The term "amnion tissue preparation" as used herein refers to a preparation of amnion tissue or amnion material. In some cases, an amnion tissue preparation can be a liquid preparation (e.g., solution or suspension) that is prepared from a dried amnion tissue preparation. The term "dried amnion tissue preparation" as used herein refers to a preparation of amnion tissue or amnion material that is dried to have a water content that is less than about 8 percent (e.g., less than about 7 percent, less than about 6 percent, less than about 5 percent, less than about 4 percent, less than about 3 percent, less than about 2 percent, or less than about 1 percent). In some cases, a dried amnion tissue preparation can have a water content that is between about 0.1 percent and about 8 percent (e.g., between about 0.5 percent and about 8 percent, between about 1 percent and about 8 percent, between about 0.1 percent and about 5 percent, between about 0.1 percent and about 4 percent, between about 0.1 percent and about 3 percent, between about 0.5 percent and about 5 percent, or between about 1 percent and about 4 percent). An amnion tissue preparation can be dried using any appropriate technique such as micronization, vacuum drying, spray drying, freeze drying, or combinations thereof. In some cases, an amnion tissue preparation can be dried as described elsewhere (e.g., U.S. Pat. No. 5,656,498).

A dried amnion tissue preparation can have any appropriate particle size. For example, a dried amnion tissue preparation can have a particle size ranging from about 0.1 µm to about 25 µm (e.g., from about 0.5 µm to about 25 µm, from about 0.75 µm to about 25 µm, from about 1 µm to about 25 µm, from about 0.1 µm to about 15 µm, from about 0.1 µm to about 10 µm, from about 0.1 µm to about 7.5 µm, from about 0.1 µm to about 5 µm, from about 0.75 µm to about 7.5 µm, or from about 1 µm to about 5 µm).

An amnion tissue preparation or a dried amnion tissue preparation can contain viable cells, non-viable cells, or a combination thereof. For example, an amnion tissue preparation or a dried amnion tissue preparation can be a preparation of amnion tissue or amnion material having viable cells. In some cases, an amnion tissue preparation can be a solution or suspension of amnion tissue or amnion material having viable cells.

In some cases, an amnion tissue preparation or a dried amnion tissue preparation can be a preparation of amnion tissue or amnion material where all the cells were removed, killed, or lysed such that the amnion tissue preparation or the dried amnion tissue preparation lacks viable cells. In some cases, an amnion tissue preparation or a dried amnion tissue preparation can be a preparation of amnion tissue or amnion material that was exposed to one or more physical and/or chemical treatments that killed, fixed, or lysed the cells of the amnion tissue or amnion material such that the amnion tissue preparation or the dried amnion tissue preparation lacks viable cells. For example, temperature (e.g., rapid freezing or rapid freezing-thawing), force and pressure, and/or electrical disruption can be used to kill or lyse cells within amnion tissue or amnion material to produce an amnion tissue preparation or a dried amnion tissue preparation that lacks viable cells.

In some cases, amnion tissue or amnion material can be obtained and then treated in a manner designed to lyse all the cells within the amnion tissue or amnion material. In these cases, the resulting material (e.g., matrix material and cellular remnants from lysed cells) can be used as an amnion tissue preparation that lacks viable cells or dried to form a dried amnion tissue preparation that lacks viable cells.

In some cases, an amnion tissue preparation or a dried amnion tissue preparation can be prepared from human amnion tissue. For example, human amnion tissue can be harvested, processed to maintain cell viability with or without removing blood, and used as an amnion tissue preparation or dried to form a dried amnion tissue preparation.

In some cases, human amnion tissue can be processed to remove blood prior to being used as an amnion tissue preparation or prior to being dried to form a dried amnion tissue preparation. In some cases, human amnion tissue can be processed without removing cells or blood prior to forming an amnion tissue preparation or a dried amnion tissue preparation.

An example of an amnion tissue preparation includes, without limitation, a human amnion tissue preparation that includes viable cells. In some cases, an amnion tissue preparation can be obtained from MiMedX® or a tissue bank (e.g., a human tissue bank).

The term "stem cell preparation" as used herein refers to a preparation of stem cells or stem cell material. In some cases, a stem cell preparation can be a liquid preparation (e.g., solution or suspension).

A stem cell preparation can contain viable stem cells, non-viable stem cells, or a combination thereof. For example, a stem cell preparation can be a preparation of viable stem cells. In some cases, a stem cell preparation can be a solution or suspension of viable stem cells.

In some cases, a stem cell preparation can be a preparation of stem cell or stem cell material where all the stem cells were killed, fixed, or lysed such that the stem cell preparation lacks viable stem cells. In some cases, a stem cell preparation can be a preparation of stem cells or stem cell material that was exposed to one or more physical and/or chemical treatments that killed, fixed, or lysed the stem cells such that the stem cell preparation lacks viable stem cells. For example, temperature (e.g., rapid freezing or rapid freezing-thawing), force and pressure, and/or electrical disruption can be used to kill or lyse stem cells to produce a stem cell preparation that lacks viable stem cells.

In some cases, a stem cell culture can be obtained and then used as a stem cell preparation in a manner that maintains stem cell viability.

Examples of stem cell preparations include, without limitation, a mesenchymal stem cell (MSC) preparation (e.g., a MSC preparation obtained from fat tissue or bone marrow), a neural stem cell (NSC) preparation (e.g., a NSC preparation obtained from a brain tissue such as striatum), an umbilical cord blood stem cell preparation, an embryonic stem cell preparation, and a human induced pluripotent stem cell preparation.

In some cases, stem cell preparations are prepared from cultures of stem cells. For example, a culture containing from about 25 million to about 25 billion stem cells can be used to make a stem cell preparation. In some cases, from about 0.1 million to about 3 million (e.g., from about 0.3 million to about 3 million, from about 0.5 million to about 3 million, from about 0.75 million to about 3 million, from about 1 million to about 3 million, from about 1.5 million to about 3 million, from about 0.3 million to about 2.5 million, from about 0.3 million to about 2.0 million, from about 0.3 million to about 1.5 million, from about 0.3 million to about 1.0 million, from about 0.5 million to about 2.5 million, from about 0.75 million to about 2.0 million, from about 0.8 million to about 1.5 million) stem cells per kg of body weight of a mammal (e.g., a human) to be treated can be used to make a stem cell preparation for administration to that mammal. In some cases, a stem cell preparation can include from about 0.025 million to about 12 million (e.g., from about 2 million to about 6 million) stem cells per kg of body weight of a mammal intended to receive the stem cell preparation. For example, when administering a stem cell preparation to a rat weighing about 250 g, a stem cell preparation can include between about 0.75 million and 1.25 million stem cells. The volume of such an administration can be from about 45 µL to about 65 µL (e.g., about 50-60 µL). These amounts and volumes can be increased appropriately for larger mammals (e.g., cats, dogs, horses, or humans). In some cases, a stem cell preparation and an amnion tissue preparation can be formulated into a single solution or suspension for administration to a mammal. For example, a dried amnion tissue preparation can be reconstituted into a solution and a stem cell preparation can be added to that solution to form a single solution or suspension having both a stem cell preparation and an amnion tissue preparation. In some cases, a stem cell preparation can be obtained commercially from a variety of suppliers such as Stemedica Cell Technologies, Inc.

Typically, a composition described herein (e.g., a composition containing an amnion tissue preparation lacking viable cells and a stem cell preparation having viable stem cells or a composition containing an amnion tissue preparation having viable cells, a stem cell preparation having viable stem cells, or both an amnion tissue preparation having viable cells and a stem cell preparation having viable stem cells) is administered via injection or infusion. For example, a composition containing an amnion tissue preparation lacking viable cells (e.g., a dried amnion tissue preparation) and a stem cell preparation having viable stem cells can be injected intravenously and/or into or near the site of a nerve injury and/or into a neurological tissue of a mammal having a neurological disorder. In some cases, a composition containing an amnion tissue preparation having viable cells and a stem cell preparation having viable stem cells can be injected into or near the site of nerve injury and/or into a neurological tissue of a mammal having a neurological disorder. In some cases, a composition described herein (e.g., a composition containing an amnion tissue preparation lacking viable cells and a stem cell preparation having viable stem cells or a composition containing an amnion tissue preparation having viable cells, a stem cell preparation having viable stem cells, or both an amnion tissue preparation having viable cells and a stem cell preparation having viable stem cells) is administered during a neurosurgical procedure.

In some cases, a composition that includes an amnion tissue preparation (e.g., an amnion tissue preparation having viable cells or an amnion tissue preparation lacking viable cells) and/or a stem cell preparation (e.g., a stem cell preparation having viable stem cells) is included in a nerve scaffold (e.g., a nerve graft or a nerve conduit). For example, a nerve scaffold including a composition containing an amnion tissue preparation lacking viable cells (e.g., a dried amnion tissue preparation) and a stem cell preparation having viable stem cells can be implanted into a mammal having a nerve injury and/or a neurological disorder. A nerve scaffold can include biological materials (e.g., blood vessels (e.g., veins, arteries, or capillaries) or skeletal muscles) or synthetic materials (e.g., silicones or polyglycolides). In some cases, a nerve scaffold including a composition containing an amnion tissue preparation having viable cells and a stem cell preparation having viable stem cells can be implanted into a mammal having a nerve injury and/or a neurological disorder. In some cases, a nerve scaffold including a composition described herein (e.g., a composition containing an amnion tissue preparation lacking viable cells and a stem cell preparation having viable stem cells or a composition containing an amnion tissue preparation having viable cells, a stem cell preparation having viable stem cells, or both an amnion tissue preparation having viable cells and a stem cell preparation having viable stem cells) is implanted during a neurosurgical procedure.

In some cases, a composition that includes an amnion tissue preparation (e.g., an amnion tissue preparation having viable cells or an amnion tissue preparation lacking viable cells) and/or a stem cell preparation (e.g., a stem cell preparation having viable stem cells) also can include one or more therapeutic agents, one or more immunosuppressant agents (e.g., corticosteroids (e.g., glucocorticoids), cytostatics, antibodies, calcineurin inhibitors, and interferons), one or more anti-inflammatory agents (e.g., non-steroidal anti-inflammatory drugs, dexamethasone or other type of glucocorticoid steroids), one or more growth factors (e.g., platelet derived growth factor PDGF, epithelial growth factor (EGF), fibroblast growth factor-2 (FGF2), or stem cell factor (SCF)), and/or one or more antimicrobial agents (e.g., antibiotics such as kanamycin, neomycin, streptomycin, or gentamicin, or an antifungal agent).

As described herein, nerve injuries and/or neurological disorders can be treated by administering (e.g., via injection such as an intravenous injection or an injection into an neurological tissue) an effective amount of a composition that includes an amnion tissue preparation described herein (e.g., an amnion tissue preparation having viable cells or an amnion tissue preparation lacking viable cells), and/or a stem cell preparation described herein (e.g., a stem cell preparation having viable stem cells). For example, compositions described herein can be used to treat a subject having a nerve injury and/or a neurological disorder, or at risk of developing a neurological disorder. In some cases, a composition can include an amnion tissue preparation (e.g., an amnion tissue preparation having viable cells or an amnion tissue preparation lacking viable cells), a NSC preparation (e.g., a stem cell preparation having viable stem cells), and one or more immunosuppressant agents (e.g., a corticosteroid). Effective amounts of compositions described herein can be determined by a physician, taking into account various factors such as overall health status, body weight, sex, diet, time and route of administration, other medications, and any other relevant clinical factors. As used herein, an "effective amount" or "therapeutically effective amount" of a composition provided herein is the amount that is sufficient to provide a beneficial effect to the subject to which the composition or preparations are delivered. The effective amount can be the amount effective to achieve a more rapid recovery, an improvement in the quality of life, or an improvement or elimination of one or more symptoms (e.g., paralysis, muscle weakness, poor coordination, loss of sensation, loss of sight, loss of speech, seizures, confusion, memory loss (e.g., short-term memory loss or long-term memory loss), pain, or altered levels of consciousness associated with a subject's nerve injury and/or neurological disorder.

In some embodiments, the methods include delivering, to the subject, an amnion tissue preparation (e.g., an amnion tissue preparation having viable cells or an amnion tissue preparation lacking viable cells) made with from about 0.01 mg to about 10 g (e.g., from about 0.01 mg to about 10 g, from about 0.1 mg to about 10 g, from about 1 mg to about 10 g, from about 10 mg to about 10 g, from about 100 mg to about 10 g, from about 1 g to about 10 g, from about 0.01 mg to about 5 g, from about 0.01 mg to about 1 g, from about 0.01 mg to about 100 mg, from about 10 mg to about 5 g, from about 100 mg to about 1 g, or from about 1 g to about 5 g) of amnion tissue per kg body weight of the subject being treated.

In some embodiments, the methods include delivering, to the subject, a stem cell preparation (e.g., a stem cell preparation having viable stem cells) made from about 0.1 million to about 3 million (e.g., from about 0.3 million to about 3 million, from about 0.5 million to about 3 million, from about 0.75 million to about 3 million, from about 1 million to about 3 million, from about 1.5 million to about 3 million, from about 0.3 million to about 2.5 million, from about 0.3 million to about 2.0 million, from about 0.3 million to about 1.5 million, from about 0.3 million to about 1.0 million, from about 0.5 million to about 2.5 million, from about 0.75 million to about 2.0 million, from about 0.8 million to about 1.5 million) stem cells per kg body weight of the subject being treated. In some cases, a stem cell preparation can include from about 0.025 million to about 12 million (e.g., from about 2 million to about 6 million) stem cells per kg of body weight of a mammal intended to receive the stem cell preparation. For example, when administering a stem cell preparation to a rat weighing about 250 g, a stem cell preparation can include between about 0.75 million and 1.25 million stem cells. The volume of such an administration can be from about 45 μL to about 65 μL (e.g., about 50-60 μL). These amounts and volumes can be increased appropriately for larger mammals (e.g., cats, dogs, horses, or humans).

In some embodiments, a composition containing an amnion tissue preparation (e.g., an amnion tissue preparation having viable cells or an amnion tissue preparation lacking viable cells) and/or a stem cell preparation (e.g., a stem cell preparation having viable stem cells) is delivered to the subject (e.g., by injection) only once. In some embodiments, multiple (e.g., two, three, four, five, six, seven, eight, nine, 10, 11, 12, 13, 14, 15, or 20 or more) administrations can be used. For example, multiple deliveries of a composition containing an amnion tissue preparation (e.g., an amnion tissue preparation having viable cells or an amnion tissue preparation lacking viable cells) and/or a stem cell preparation (e.g., a stem cell preparation having viable stem cells) can be made over the course of several (e.g., two, three, four, five, six, seven, eight, nine, 10, 14, 21, 28, or 31 or more) consecutive days (e.g., one delivery each day for seven days or one delivery every other day for seven days). In some cases, a composition containing an amnion tissue preparation (e.g., an amnion tissue preparation having viable cells or an amnion tissue preparation lacking viable cells) and/or a stem cell preparation (e.g., a stem cell preparation having viable stem cells) can be delivered from about once a week to about once per year (e.g., once every month or once every other month). In some cases, a composition containing an amnion tissue preparation (e.g., an amnion tissue preparation having viable cells or an amnion tissue preparation lacking viable cells) and/or a stem cell preparation (e.g., a stem cell preparation having viable stem cells) can be delivered to a subject for several months (e.g., one delivery per month for six months, or one delivery per week for two months).

A composition containing an amnion tissue preparation (e.g., an amnion tissue preparation having viable cells or an amnion tissue preparation lacking viable cells) and/or a stem cell preparation (e.g., a stem cell preparation having viable stem cells) can be delivered to a subject at various time points after diagnosis with a nerve injury and/or a neurological disorder. For example, a composition containing an amnion tissue preparation (e.g., an amnion tissue preparation having viable cells or an amnion tissue preparation lacking viable cells) and/or a stem cell preparation (e.g., a stem cell preparation having viable stem cells) can be delivered immediately following diagnosis with a nerve injury and/or a neurological disorder. In some cases, a composition containing an amnion tissue preparation (e.g., an amnion tissue preparation having viable cells or an amnion tissue preparation lacking viable cells) and/or a stem cell preparation (e.g., a stem cell preparation having viable stem cells) can be delivered to a subject less than 10 (e.g., 9, 8, 7, 6, 5, 4, 3, 2, or 1) days after diagnosis with a nerve injury and/or a neurological disorder.

The subject treated as described herein can be any mammal, e.g., a human (e.g., a human patient) or a non-human primate (e.g., chimpanzee, baboon, or monkey), a mouse, a rat, a rabbit, a guinea pig, a gerbil, a hamster, a horse, a camel, a type of livestock (e.g., cow, pig, sheep, or goat), a mammalian zoo animal (e.g., a lion, a tiger, or a leopard), a dog, or a cat.

A composition containing an amnion tissue preparation (e.g., an amnion tissue preparation having viable cells or an amnion tissue preparation lacking viable cells) and/or a stem cell preparation (e.g., a stem cell preparation having viable stem cells) can be administered to a subject as a combination therapy with another treatment used to treat a nerve injury and/or a neurological disorder. For example, a combination therapy can include administering to the subject (e.g., a human patient) one or more additional agents that provide a therapeutic benefit to the subject who has a nerve injury and/or neurological disorder, or is at risk of developing a neurological disorder. In some cases, the composition and the one or more additional agents can be administered at the same time. In some cases, the composition can be administered first, and the one or more additional agents administered second, or vice versa.

The efficacy of a given treatment in treating a nerve injury and/or a neurological disorder can be defined as an improvement of one or more symptoms of the nerve injury and/or the neurological disorder by at least 5% (e.g., at least 10%, at least 15%, at least 20%, at least 25%, at least 30%, at least 40%, at least 50%, at least 55%, at least 60%, at least 65% or more). In some cases, efficacy of a treatment with a composition containing an amnion tissue preparation (e.g., an amnion tissue preparation having viable cells or an amnion tissue preparation lacking viable cells) and/or a stem cell preparation (e.g., a stem cell preparation having viable stem cells) can be determined from the stabilization of one or more symptoms associated with the nerve injury and/or the neurological disorder (i.e., the treatments curtail the worsening of one or more symptoms of the nerve injury and/or the neurological disorder).

In some cases, the methods described herein can include monitoring a nerve injury and/or a neurological disorder in the subject to, for example, determine if the nerve injury and/or the neurological disorder is improving with treatment. Any appropriate method can be used to monitor the nerve injury and/or the neurological disorder. For example, cognitive impairment can be monitored, physical impairment can be monitored, pain can be monitored, medical imaging (e.g., neuroimaging using computer assisted tomography (CAT scans), magnetic resonance imaging (MRIs), and/or X-rays) can be performed.

A composition containing an amnion tissue preparation (e.g., an amnion tissue preparation having viable cells or an amnion tissue preparation lacking viable cells) and/or a stem cell preparation (e.g., a stem cell preparation having viable stem cells) can be combined with packaging material and sold as a kit. The packaging material included in a kit typically contains instructions or a label describing how the composition can be administered via, for example, injection such as an intravenous injection or an injection into or near one or more neurological tissues (e.g., brain, spinal cord, cranial nerves, peripheral nerves, nerve roots, and/or neuromuscular junctions). A kit also can include a unit dose injector. The term "unit dose injector" refers to an injection device that delivers a single dose of a composition containing an amnion tissue preparation (e.g., an amnion tissue preparation having viable cells or an amnion tissue preparation lacking viable cells) and/or a stem cell preparation (e.g., a stem cell preparation having viable stem cells) by injection into a user. Typically, a unit dose injector contains a single container that holds or contains an injectable formulation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nerve scaffold comprising:
 a blood vessel conduit selected from a vein or an artery; and
 a composition comprising a stem cell preparation having viable cells and an amnion tissue preparation wherein the amnion tissue preparation lacks viable cells,
 wherein the composition is inside the conduit.

2. The nerve scaffold of claim 1, wherein said blood vessel conduit is a vein.

3. The nerve scaffold of claim 1, wherein said blood vessel conduit is an artery.

4. The nerve scaffold of claim 1, wherein said stem cell preparation is a human mesenchymal stem cell preparation.

5. The nerve scaffold of claim 1, wherein said stem cell preparation is a human neural stem cell preparation.

6. The nerve scaffold of claim 1, further comprising a therapeutic agent, an immunosuppressant agent, or a pharmaceutical excipient.

7. The nerve scaffold of claim 1, wherein said composition comprises from about 5 mg and about 5 g of said amnion tissue preparation.

8. A method of treating a nerve injury or a neurological disorder in a mammal, said method comprising implanting, to said mammal the nerve scaffold of claim 1, wherein a symptom of said nerve injury or neurological disorder is improved.

9. The method of claim 8, wherein said mammal is a human, dog, or horse.

10. The method of claim 8, wherein said method comprises treating said nerve injury, and said nerve injury is a spinal cord injury or a peripheral nerve injury.

11. The method of claim 10, wherein said nerve injury is a partially or fully severed nerve.

12. The method of claim 1, wherein said method comprises treating said neurological disorder, and said neurological disorder is selected from the group consisting brain trauma, stroke, and dementia.

13. The method of claim 8, wherein said amnion tissue preparation comprises an amnion tissue preparation prepared from about 1 mg to about 10 g of amnion tissue per kg of body weight of said mammal.

14. The method of claim 8, wherein said amnion tissue preparation is a human amnion tissue preparation.

15. The method of claim 8, wherein said stem cell preparation is a human mesenchymal stem cell preparation.

16. The method of claim 8, wherein said stem cell preparation is a human neural stem cell preparation.

* * * * *